United States Patent
Harrison et al.

(10) Patent No.: US 11,795,194 B2
(45) Date of Patent: Oct. 24, 2023

(54) METHOD OF PURIFYING PHYCOCYANIN

(71) Applicant: UNIVERSITY OF CAPE TOWN, Cape Town (ZA)

(72) Inventors: Susan Thérèse Largier Harrison, Cape Town (ZA); Matthew Armstrong Burke, Cape Town (ZA); Robert William McClelland Pott, Stellenbosch (ZA); Marijke Antonia Fagan-Endres, Cape Town (ZA)

(73) Assignee: University of Cape Town, Cape Town (ZA)

( * ) Notice: Subject to any disclaimer, the term of this patent is extended or adjusted under 35 U.S.C. 154(b) by 491 days.

(21) Appl. No.: 16/639,250

(22) PCT Filed: Aug. 2, 2018

(86) PCT No.: PCT/IB2018/055809
§ 371 (c)(1),
(2) Date: Feb. 14, 2020

(87) PCT Pub. No.: WO2019/034955
PCT Pub. Date: Feb. 21, 2019

(65) Prior Publication Data
US 2020/0255473 A1 Aug. 13, 2020

(30) Foreign Application Priority Data

Aug. 18, 2017 (GB) ..................... 1713293

(51) Int. Cl.
| | | |
|---|---|---|
| C07K 1/36 | (2006.01) | |
| C07K 1/14 | (2006.01) | |
| C07K 1/30 | (2006.01) | |
| C07K 14/195 | (2006.01) | |
| C07K 14/405 | (2006.01) | |

(52) U.S. Cl.
CPC .............. *C07K 1/36* (2013.01); *C07K 1/145* (2013.01); *C07K 1/303* (2013.01); *C07K 14/195* (2013.01); *C07K 14/405* (2013.01)

(58) Field of Classification Search
None
See application file for complete search history.

(56) References Cited

FOREIGN PATENT DOCUMENTS

| CN | 102993297 A | 3/2013 |
|---|---|---|
| EP | 0 180 567 A2 | 5/1986 |
| IN | 18/2005 | 5/2005 |

OTHER PUBLICATIONS

Rito-Palomares, M., et al. 2001 J Chem Technol Biotechnol 76: 1273-1280. (Year: 2001).*
Hatti-Kaul, R. Aqueous Two-Phase Systems: A General Overview in Methods in in Biotechnology vol. 11: Aqueous Two-Phase Systems: Methods and Protocols, edited by R. Hatti-Kaul, 2000: pp. 1-10. (Year: 2000).*
Narayan, N.V., et al. 2007 International Journal of Food Engineering 3(4): article 16, 19 pages. (Year: 2007).*
Rahman, D.Y., et al. 2017 J Appl Phycol 29: 1233-1239, published online Nov. 21, 2016. (Year: 2016).*
Saran, S., et al. 2016 IJAPSA 2(3): 15-20. (Year: 2016).*
Albertsson, Per-Aake, "The contribution of photosynthetic pigments to the development of biochemical separation methods: 1900-1980," Photosynthesis Research; Official Journal of the International Society of Photosynthesis Research, Springer, Berlin, Jun. 1, 2003, vol. 76, No. 1-3, pp. 217-225.
Chavez-Santoscoy, A. et al., "Application of aqueous two-phase systems for the potential extractive fermentation of cyanobacterial products," Chemical Engineering and Technology, Jan. 1, 2010, vol. 33, No. 1, pp. 177-182.
International Search Report dated Oct. 19, 2018, PCT Application No. PCT/IB2018/055809, 3 pages.
Mayolo-Deloisa, Karla et al., "Case studies in the application of aqueous two-phase processes for the recovery of high value biological products," In: Development in Biotechnology and Bioprocessing, Mar. 8, 2013, pp. 33-50.
Patil, G., "Aqueous two phase extraction for purification of C-phycocyanin," Biochemical Engineering Journal, May 2007, vol. 34, Issue 2, pp. 156-164.
Rito-Palomares, Marco et al., "Practical application of aqueous two-phase partition to process development for the recovery of biological products," Journal of Chromatography B, Jul. 25, 2004, vol. 807, Issue 1, pp. 3-11.
Szlag, D. et al., "A low-cost aqueous two phase system for enzyme extraction," Biotechnology Techniques, 1988, vol. 2, No. 4, pp. 277-282.
UK Intellectual Property Office Search Report dated Sep. 29, 2017, Application No. GB1713293.7, 5 pages.

\* cited by examiner

*Primary Examiner* — Marsha Tsay
(74) *Attorney, Agent, or Firm* — Knobbe, Martens, Olson & Bear, LLP

(57) ABSTRACT

A method for purifying phycocyanin from a phycocyanin-containing solution is provided. The method comprises a first step of partially purifying the solution by aqueous two-phase separation (ATPS) and a second step of purifying the phycocyanin by ammonium sulfate precipitation. The purified phycocyanin product can in some cases be of a sufficiently pure grade to be used as a food or cosmetic pigment.

18 Claims, 3 Drawing Sheets

METHOD OF PURIFYING PHYCOCYANIN

CROSS-REFERENCE(S) TO RELATED APPLICATIONS

This application claims priority from United Kingdom patent application number 1713293.7 filed on 18 Aug. 2017, which is incorporated by reference herein.

FIELD OF THE INVENTION

The invention relates to a method for purifying phycocyanin from a biomass.

BACKGROUND TO THE INVENTION

Phycocyanin extracted from biological sources such as plants, algae, cyanobacteria, bacteria or fungi, is a one of the few pigments that can be used as a natural food and cosmetic colouring.

Furthermore, it has nutritional benefits due to its immune enhancing, anti-inflammatory and anti-oxidant properties and in its purer forms is used for immunodiagnostics and analytical applications due to its fluorescent properties. Phycocyanin has relatively recently been approved as a food additive in both the USA, where it is exempt from certification, and by the EU, where it does not require an E number (usually required for food additive certification). The pigment is also relatively stable and easy to dissolve. There is a considerable market for phycocyanin which it is estimated will grow significantly. As such the design of an effective production process for phycocyanin is highly sought after to match this market size and expected growth.

Current methods for extracting and purifying phycocyanin from a biomass include vacuum distillation, ammonium sulfate precipitation, ultrafiltration, adsorption and various chromatographic purification methods. The problems with the current processing methods include: time-consuming processing steps, the large number of processing steps required, the expense of scale-up and the impact that bacterial and other contamination, incoming with the biological substrate, has on the final product.

Numerous prior art documents describe the use of aqueous two-phase separation (ATPS) for the extraction of phycocyanin from cyanobacteria. Almost all of these describe a polyethylene glycol (PEG)-salt ATPS system which is selected so that the phycocyanin partitions to the PEG top phase. In these processes the recovery of phycocyanin from the PEG phase is almost exclusively achieved through the use of ultrafiltration due to the PEG-protein complexes formed and the difficulty of protein recovery. The use of adsorption, dialysis and ammonium sulfate precipitation either alone or with ultrafiltration is also considered in some of the processes. These processes are often characterised by time-consuming processing steps, expensive scale-up and low product purity.

There is therefore a need for a method of isolating phycocyanin from a biological source which addresses the above-mentioned problems, at least to some extent.

In this specification the term "biomass" shall have its widest meaning and denote organic material which may be in a natural or processed state and which may be obtained from biological sources such as plants, algae, cyanobacteria, bacteria or fungi.

Furthermore, unless the contents requires otherwise the word 'comprise' or variations such as 'comprises' or 'comprising' will be understood to imply the inclusion of a stated integer or group of integers but not the exclusion of any other integer or group of integers.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a method for purifying phycocyanin from a phycocyanin-containing solution, the method comprising contacting the solution with an aqueous two-phase mixture which includes a polyethylene glycol (PEG)-containing phase and a carbohydrate-containing phase in which conditions are selected to permit the phycocyanin to partition to the carbohydrate-containing phase, separating the carbohydrate-containing phase from the PEG-containing phase, treating the carbohydrate-containing phase with ammonium sulfate to form a precipitating solution in which the phycocyanin is precipitated, and recovering the precipitated phycocyanin.

The concentration of ammonium sulfate in the precipitating solution may be from 14 to 36 wt %.

The method may further comprise dissolving the precipitated phycocyanin in solution, treating the solution with ammonium sulfate to form a second precipitating solution in which the phycocyanin is re-precipitated, and recovering the re-precipitated phycocyanin.

The concentration of ammonium sulfate in the second precipitating solution may be from 25 to 34 wt %.

The method may further comprise re-dissolving the re-precipitated phycocyanin in a second solution, treating the re-dissolved phycocyanin with ammonium sulfate to form a third precipitating solution in which the phycocyanin is re-precipitated, and recovering the re-precipitated phycocyanin.

The concentration of ammonium sulfate in the third precipitating solution may be from 16 to 28 wt %.

The PEG may have an average molecular weight of at least 6000 g/mol, or at least 10,000 g/mol, and may be present in the PEG-containing phase at a concentration of from about 3 to 15 wt %.

The carbohydrate may be present in the carbohydrate-containing phase at a concentration of from about 15 to 40 wt %, the carbohydrate may have a dextrose equivalent of from 10 to 20, and the carbohydrate may be selected from the group consisting of: maltodextrin, ficoll, dextran, starch, glucose, fructose, galactose, mannose, sucrose, cellobiose, lactose, lactulose, maltose, maltulose, arabinose, ribose, xylose and trehalose.

The overall two-phase mixture may comprise 15-40 wt %, preferably about 30 wt % of the carbohydrate-containing phase; 3-15 wt %, preferably about 5 wt % of the PEG-containing phase; and 45-82 wt % of the phycocyanin-containing solution.

The phycocyanin-containing solution may be prepared as a cell extract from wet or dry biomass, the biomass may be obtained from plants, algae, cyanobacteria, bacteria or fungi, and the biomass may be obtained from *Spirulina*.

The phycocyanin may be C-phycocyanin.

An embodiment of the invention will now be described, by way of example only, with reference to the accompanying figures.

DETAILED DESCRIPTION OF THE INVENTION

Figure 1:
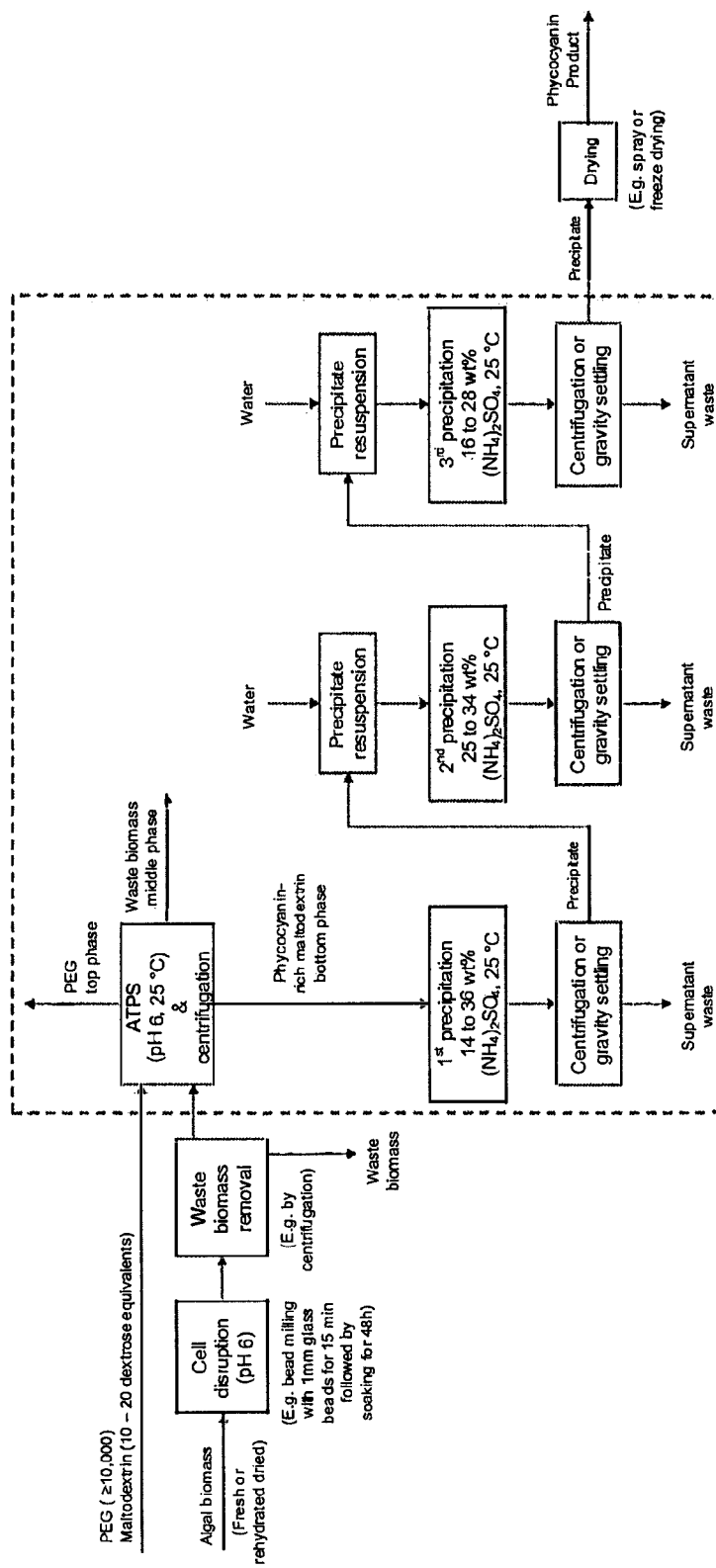
FIG. 1 is a flow diagram illustrating an embodiment of the method.

A method for purifying phycocyanin from a phycocyanin-containing solution is provided. The phycocyanin may be C-phycocyanin, R-phycocyanin or allophycocyanin, but is preferably C-phycocyanin.

The method comprises contacting the phycocyanin-containing solution with an aqueous two-phase mixture forming an aqueous two-phase system (ATPS) and which includes a polyethylene glycol (PEG)-containing aqueous phase and a carbohydrate-containing aqueous phase in which conditions are selected to permit the phycocyanin to partition to the carbohydrate-containing phase. The conditions can be selected from temperature, concentration and pH of each of the phases. The two phases are mixed and then caused or allowed to settle by centrifugation or gravity settling, or by any other suitable method. The carbohydrate-containing aqueous phase is separated from the PEG-containing aqueous phase and treated with ammonium sulfate to form a precipitating solution in which the phycocyanin is precipitated. The precipitated phycocyanin is then recovered.

The PEG in the PEG-containing aqueous phase can have an average molecular weight of at least 6000 g/mol, 7000 g/mol, 8000 g/mol, 9000 g/mol, or at least 10,000 g/mol. The PEG can be present in the PEG-containing aqueous phase at a concentration of from about 3 to 15 wt %. Here and elsewhere in the present disclosure, the weight percent (wt %) units indicate weight (in grams) of solute (which can be ammonium sulfate, PEG, carbohydrate or phycocyanin, depending on the context) per 100 millilitres of water.

The carbohydrate can be present in the carbohydrate-containing phase at a concentration of from about 15 to 40 wt %, and the carbohydrate can be selected from the group consisting of: maltodextrin, ficoll, dextran, starch, glucose, fructose, galactose, mannose, sucrose, cellobiose, lactose, lactulose, maltose, maltulose, arabinose, ribose, xylose, and trehalose. In some embodiments, the carbohydrate has a dextrose equivalent of from 10 to 20.

The overall two-phase mixture may comprise 15-40 wt %, preferably about 30 wt %, of the carbohydrate-containing phase; 3-15 wt %, preferably about 5 wt %, of the PEG-containing phase; and 45-82 wt % of the phycocyanin-containing solution. The weight percent (wt %) units here refer to the weight of the phase as a percentage of the total weight of the two-phase mixture. The sum of the weight percentages of the carbohydrate-containing phase, PEG-containing phase and phycocyanin-containing solution is approximately 100 percent.

The method can be performed on any suitable phycocyanin-containing solution, which is typically a cell extract. The cell extract can be prepared from wet or dried biomass obtained from plants, algae, cyanobacteria, bacteria or fungi. The cell extract is preferably prepared from fresh or rehydrated dried algal or cyanobacterial biomass. *Spirulina* is a particularly suitable biomass type as it has a high phycocyanin content and is non-toxic to humans. This is important where the phycocyanin is to be used as a food or cosmetic additive for humans. The cell extract is preferably clarified before contacting the aqueous two-phase mixture or ATPS. In some embodiments, the cells can be disrupted in aqueous solution at a pH of from about 4 to 8, preferably at about pH 6, by bead milling, although any suitable cell rupture method may be used. Further suitable cell rupture methods include, amongst others, physical cell rupture, high pressure homogenisation, sonication or cryopulverisation. The ruptured cells can then be left to soak to allow the phycocyanin to leach into the solution.

The resulting crude mixture can be clarified by centrifugation, filtration, tangential filtration or any other suitable means, and the aqueous extract contacted by the two aqueous phases in the ATPS. The ATPS separates the phycocyanin from residual biomass in the extract and removes microbial and protein contamination which may be present in the feedstock. The entire method may be carried out at a convenient temperature of about 25° C. without resulting in significant loss of yield, although the method can equally be performed at any ambient temperature of from about 4° C. to about 50° C.

The final concentration of ammonium sulfate in the precipitating solution may be from about 14 to 36 wt %, typically about 23 wt %, which is equivalent to a 25 to 80% saturation ammonium sulfate solution. For clarity purposes and in order to avoid ambiguity, the "% saturation" concentration is based on the combined total volume of the ammonium sulfate solution and phycocyanin-containing phase and indicates the extent of saturation of the combined solution based on a 100% saturated ammonium sulfate solution. The ammonium sulfate may be added to the precipitating solution in the form of an aqueous solution, or alternatively, it may be added in solid form and subsequently dissolved. The precipitated phycocyanin can be collected by centrifugation, gravity settling, filtration or tangential filtration.

As shown in FIG. 1, the method can include one or more additional ammonium sulfate precipitation steps to enhance the purity of the isolated phycocyanin. A second ammonium sulfate precipitation can be carried out by dissolving the precipitated phycocyanin in solution, treating the solution with ammonium sulfate to form a second precipitating solution in which the phycocyanin is re-precipitated, and recovering the re-precipitated phycocyanin. The concentration of ammonium sulfate in the second precipitating solution can be from 25 to 34 wt %, typically about 29 wt %, which is equivalent to a 55 to 75% saturation ammonium sulfate solution. The re-precipitated phycocyanin can be recovered by centrifugation, gravity settling, filtration or tangential filtration.

A third ammonium sulfate precipitation can be carried out by re-dissolving the re-precipitated phycocyanin in solution, treating the solution with ammonium sulfate to form a third precipitating solution in which the phycocyanin is re-precipitated, and isolating the purified re-precipitated phycocyanin. The concentration of ammonium sulfate in the third precipitating solution can be from about 16 to 28 wt %, typically about 18 wt %, which is equivalent to a 35 to 60% saturation ammonium sulfate solution. The precipitated phycocyanin can be recovered by centrifugation, gravity settling, filtration or tangential filtration, and thereafter dried. The carbohydrate in the solution stabilises the phycocyanin and allows for spray- or freeze-drying without major denaturing of the phycocyanin protein. Other drying methods may also be used.

As illustrated in the accompanying figures, the purity of the phycocyanin produced by the present method increases with an increase in the number of ammonium sulfate precipitation stages. The precipitation stages purify the phycocyanin by removing contaminating proteins and simultaneously removing microbial contamination. Ammonium sulfate precipitation without the ATPS does not give the required purity grade of product, whereas extracting the phycocyanin directly after the ATPS does not sufficiently reduce the microbial contamination. The desired level of purity can only be obtained by combining ATPS with ammonium sulfate precipitation.

Figure 2:
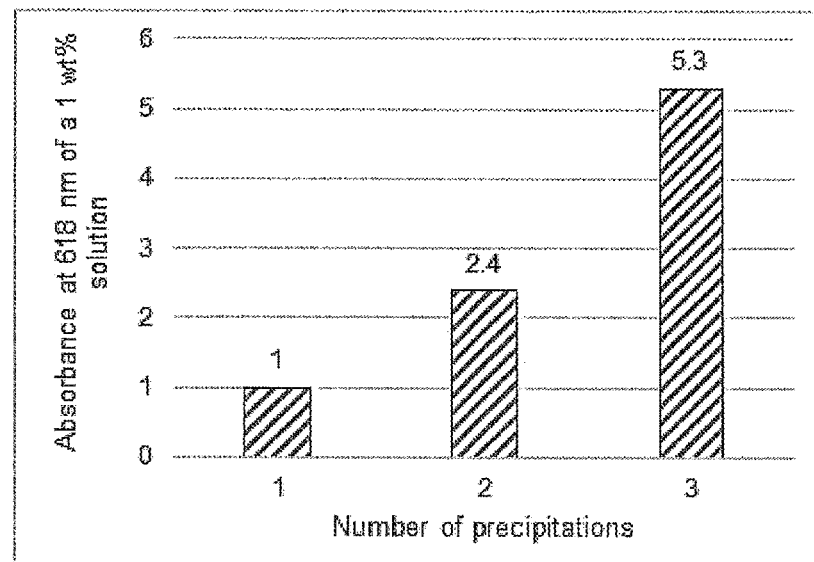
FIG. 2 is graph illustrating the effect of the ammonium sulfate precipitation stages on the purity of phycocyanin produced in terms of the E number.
Figure 3:
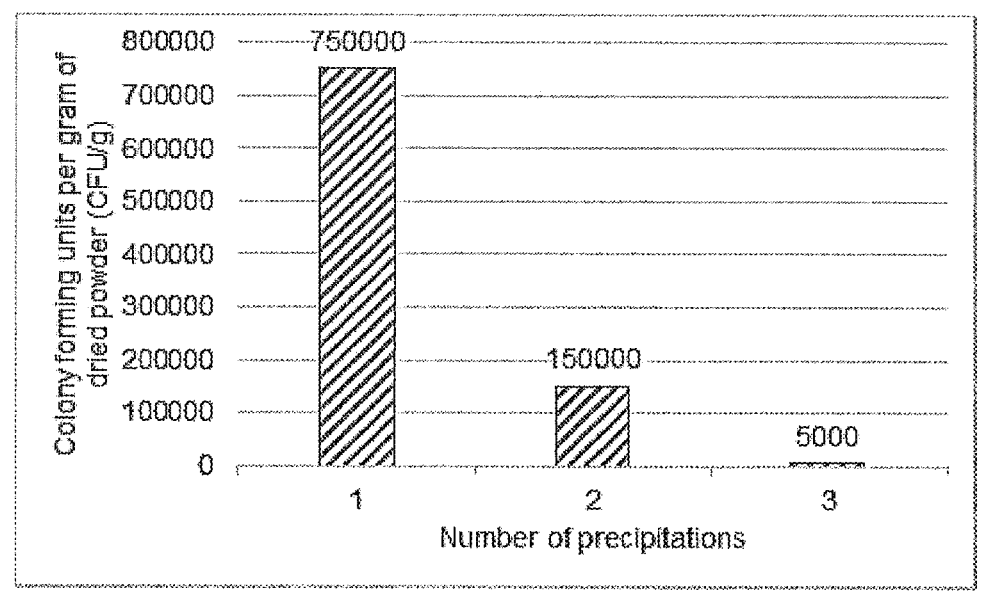
FIG. 3 is a graph illustrating the effect of ammonium sulfate precipitation on the microbial contamination of dried phycocyanin powder isolated according to the method.
Figure 4:
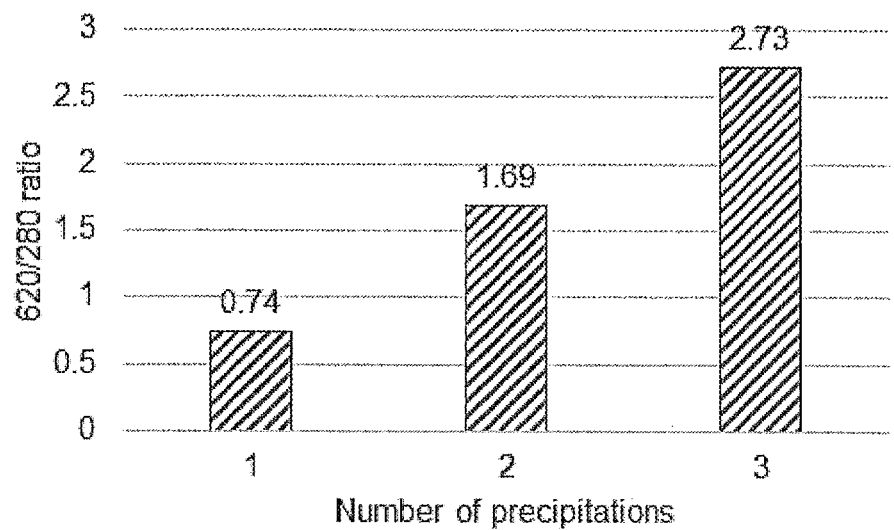
FIG. 4 is a graph illustrating the effect of ammonium sulfate precipitation stages on the 620/280 purity ratio.
Figure 5:
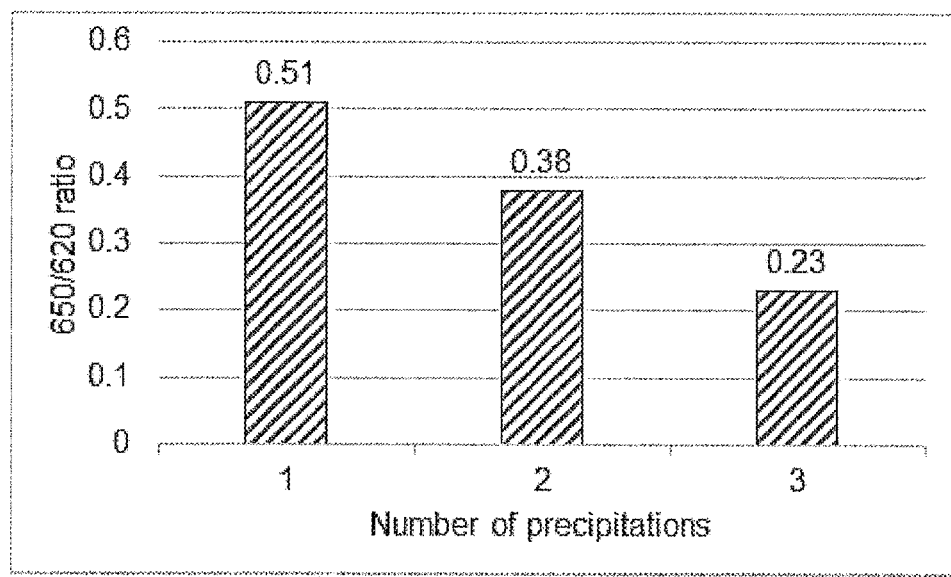
FIG. 5 is a graph illustrating the effect of ammonium sulfate precipitation stages on the 650/620 purity ratio.

The improvement in phycocyanin purity is shown in FIG. 2 through the increase in the E number with each successive precipitation from 1 (below food grade) to over 5 (food grade). The E number in the context of purification indicates the purity of phycocyanin and is measured by the absorbance at 618 nm of a 1 wt % solution. The reduction in microbial contamination with each successive precipitation is shown in FIG. 3 and is measured by the number of colony forming units per gram of dried powder (CFU/g). The improvement in the 620/280 nm (phycocyanin to total protein) purity ratio with each successive precipitation is shown in FIG. 4 with the first precipitation producing low quality food grade phycocyanin, while the third precipitation produced a ratio of greater than 1.5, which is consistent with cosmetic grade phycocyanin. The improvement in the 650/620 nm ratio is shown in FIG. 5 and demonstrates that each subsequent precipitation purified the product to have a greater ratio of C-phycocyanin to allophycocyanin. The 650/620 ratio of less than 0.3 produced after three precipitations is consistent with cosmetic and even reagent grade phycocyanin. The present method produces phycocyanin of food grade or higher with minimal microbial contamination and advantageously avoids the use of expensive equipment such as chromatography and vacuum distillation apparatuses that are commonly used in the art. This method is also capable of being performed in a considerably shorter time than conventional chromatography, distillation or ATPS methods used to extract phycocyanin.

The invention will now be described in further detail by way of the following non-limiting example.

EXAMPLE

A 3 L vessel was filled with 1 kg of 1 mm glass beads and agitated with an overhead stirrer operated at 180 RPM. Cyanobacterial feedstock, in this embodiment *Spirulina* (100 g dry or 900 g wet), was loaded and a mixture (92% sodium citrate, 8% citric acid) of citrate salts added to obtain a 5 g/L buffering capacity at pH 6 and topped up to 1 L with water. Optimal phycocyanin recovery was obtained by milling the cyanobacteria for 15 minutes and then allowing it to soak for 48 hours to allow for phycocyanin to leach into solution. pH was found to be important for optimising phycocyanin extraction, with values below 4 and above 8 resulting in decreased yields. Therefore buffering at pH 6 was important. Cyanobacterial loading and bead material (glass or steel) were not found to affect phycocyanin production. 1 mm beads resulted in the best extraction compared to larger sizes.

The waste biomass was removed using a batch centrifuge, operated at 7000 g for 20 minutes. Following centrifugation, the supernatant was carefully poured off and the biomass pellet discarded. This batch centrifugation approach was well suited to the lab-scale operation. Tangential filtration may also be a viable alternative to centrifugation, but dead-end filtration was found to be ineffective due to the quick build-up of the biomass debris.

An aqueous two phase system (ATPS) which included a 15-40 wt % maltodextrin-containing aqueous phase, which in some examples contained 30 wt % maltodextrin, and a 3-15 wt % PEG-containing aqueous solution, which in some examples contained 5 wt % PEG, was employed for the separation. The PEG-containing aqueous solution had an average PEG molecular weight of 10 000 g/mol or more. The phycocyanin-containing aqueous supernatant from the biomass milling made up the remaining wt %. The two-phase mixture and phycocyanin-containing supernatant were vigorously agitated to achieve complete mixing before separation of the two-phases was achieved by centrifugation or gravity settling. The phycocyanin rich maltodextrin bottom layer was then removed for further processing.

The ATPS was conveniently operated at an ambient temperature of about 25° C. The pH was not altered from the milling and waste biomass removal stage, and was performed at about pH 6.

The molecular weight of the PEG was used to select whether the phycocyanin partitioned to the maltodextrin or PEG layer. Investigation showed that while PEG 6000, PEG 7000, PEG 8000, and PEG 9000 were suitable for use in the method, PEG 10,000 or higher resulted in the best recoveries of phycocyanin to the maltodextrin layer, thus avoiding the PEG-protein complexes that result from some aqueous two-phase systems and which make subsequent recovery of the phycocyanin difficult. The maltodextrin forms complexes with the phycocyanin but these complexes are weakly bonded and as such the phycocyanin can be precipitated more easily than PEG-phycocyanin complexes. An ATPS containing 30 wt % maltodextrin and 5 wt % PEG 10,000 was found to be optimal for the recovery of phycocyanin.

The phycocyanin solution from the ATPS was treated with ammonium sulfate (14-36 wt %) and the mixture left to stand for a minimum of one hour before being centrifuged at 7000 g. The clear liquid supernatant was subsequently removed by suction. The remaining cell pellet was then re-dissolved in water to 80% of the initial volume and treated with 25-34 wt % ammonium sulfate. The mixture was left to stand for a minimum of one hour before being centrifuged at 7000 g. The clear supernatant was removed by suction and the pellet re-dissolved in water to 80% of the initial volume. The solution was again treated with ammonium sulfate (16-28 wt %) and left to stand for at least one hour before being centrifuged at 7000 g. After removal of the clear supernatant, the precipitate was spray- or freeze-dried to yield a highly purified phycocyanin product.

The invention claimed is:

1. A method for purifying phycocyanin from a phycocyanin-containing solution, the method comprising:
   a) contacting the solution with an aqueous two-phase mixture which includes a polyethylene glycol (PEG)-containing phase and a carbohydrate-containing phase in which conditions are selected to permit the phycocyanin to partition to the carbohydrate-containing phase,
   b) separating the carbohydrate-containing phase from the PEG-containing phase,
   c) treating the carbohydrate-containing phase with ammonium sulfate to form a first precipitating solution in which the phycocyanin is precipitated,
   d) recovering a precipitated phycocyanin,
   e) dissolving the precipitated phycocyanin in a solution and treating the solution with ammonium sulfate to form a second precipitating solution in which the phycocyanin is re-precipitated, f) recovering a second precipitated phycocyanin, and g) if the second precipitated phycocyanin has a purity lower than food grade, repeating steps e) and f) to obtain a third precipitated phycocyanin, wherein the second or third precipitated phycocyanin has a purity of food grade or higher after one round of aqueous two-phase separation and wherein no ultrafiltration step is performed on the carbohydrate-containing phase before it is treated with ammonium sulfate.

2. The method of claim 1, wherein the concentration of ammonium sulfate in the first precipitating solution is from 14 to 36 wt %.

3. The method of claim 1, wherein the concentration of ammonium sulfate in the second precipitating solution is from 25 to 34 wt %.

4. The method of claim 1, further comprising re-dissolving the second precipitated phycocyanin, treating with ammonium sulfate to form a third precipitating solution in which the phycocyanin is re-precipitated, and recovering a third precipitated phycocyanin.

5. The method of claim 4, wherein the concentration of ammonium sulfate in the third precipitating solution is from 16 to 28 wt %.

6. The method of claim 1, wherein the PEG has an average molecular weight of at least 6000 g/mol.

7. The method of claim 6, wherein the PEG has an average molecular weight of at least 10,000 g/mol.

8. The method of claim 1, wherein the carbohydrate is present in the carbohydrate-containing phase at a concentration of from about 15 to 40 wt %.

9. The method of claim 1, wherein the carbohydrate is selected from the group consisting of: maltodextrin, ficoll, dextran, starch, glucose, fructose, galactose, mannose, sucrose, cellobiose, lactose, lactulose, maltose, maltulose, arabinose, ribose, xylose, and trehalose.

10. The method of claim 1, wherein the overall two-phase mixture includes 15-40 wt % of the carbohydrate-containing phase, 3-15 wt % of the PEG-containing phase and 45-82 wt % of the phycocyanin-containing solution.

11. The method of claim 1, wherein the phycocyanin-containing solution is a cell extract.

12. The method of claim 11, wherein the cell extract is prepared from wet biomass, wherein the biomass is obtained from *Spirulina*.

13. The method of claim 1, wherein the phycocyanin is C-phycocyanin.

14. The method of claim 1, wherein the first precipitated phycocyanin has a purity of cosmetic grade or higher after one aqueous two-phase separation step and without an ultrafiltration step being performed on the carbohydrate-containing phase.

15. The method of claim 1, wherein only one aqueous two-phase separation step is performed on the phycocyanin-containing solution.

16. The method of claim 1, wherein the carbohydrate-containing phase is treated with ammonium sulfate directly after having been separated from the PEG-containing phase.

17. The method of claim 1, wherein:

only one aqueous two-phase separation step is performed on the phycocyanin-containing solution; and the carbohydrate-containing phase is treated with ammonium sulfate directly after having been separated from the PEG-containing phase.

18. The method of claim 1, wherein:

the PEG in the PEG-containing phase has an average molecular weight of at least 6,000 g/mol (PEG 6,000);

only one aqueous two-phase separation step is performed on the phycocyanin-containing solution; and the carbohydrate-containing phase is treated with ammonium sulfate directly after having been separated from the PEG-containing phase.

\* \* \* \* \*